United States Patent
Park et al.

(10) Patent No.: US 11,096,667 B2
(45) Date of Patent: Aug. 24, 2021

(54) ULTRASOUND IMAGING APPARATUS AND METHOD OF CONTROLLING THE SAME

(71) Applicant: SAMSUNG ELECTRONICS CO., LTD., Suwon-si (KR)

(72) Inventors: Jong-geun Park, Seoul (KR); Ho-kyung Kang, Seoul (KR); Jung-ho Kim, Yongin-si (KR)

(73) Assignee: SAMSUNG MEDISON CO., LTD., Hongcheon-gun (KR)

( * ) Notice: Subject to any disclaimer, the term of this patent is extended or adjusted under 35 U.S.C. 154(b) by 235 days.

(21) Appl. No.: 15/814,708

(22) Filed: Nov. 16, 2017

(65) Prior Publication Data
US 2018/0132828 A1    May 17, 2018

(30) Foreign Application Priority Data
Nov. 17, 2016    (KR) .................. 10-2016-0153317

(51) Int. Cl.
    *A61B 8/00*      (2006.01)
    *A61B 8/08*      (2006.01)

(52) U.S. Cl.
CPC .............. *A61B 8/465* (2013.01); *A61B 8/085* (2013.01); *A61B 8/0891* (2013.01); *A61B 8/463* (2013.01); *A61B 8/469* (2013.01); *A61B 8/481* (2013.01); *A61B 8/54* (2013.01); *A61B 8/4472* (2013.01); *A61B 8/464* (2013.01); *A61B 8/466* (2013.01); *A61B 8/5207* (2013.01); *A61B 8/565* (2013.01)

(58) Field of Classification Search
CPC ................................ A61B 8/085; A61B 8/469
See application file for complete search history.

(56) References Cited

U.S. PATENT DOCUMENTS

| | | | |
|---|---|---|---|
| 8,460,194 B2 | 6/2013 | Averkiou et al. | |
| 9,164,171 B2 | 10/2015 | Park et al. | |
| 9,483,821 B2 | 11/2016 | Oh et al. | |
| 2006/0210131 A1* | 9/2006 | Wheeler, Jr. .......... | G06T 11/008 382/128 |
| 2011/0208061 A1 | 8/2011 | Chang | |
| 2013/0030278 A1* | 1/2013 | Seong .................. | G06T 7/0012 600/407 |

(Continued)

FOREIGN PATENT DOCUMENTS

| | | |
|---|---|---|
| CN | 102209495 A | 10/2011 |
| CN | 104799882 A | 7/2015 |

(Continued)

OTHER PUBLICATIONS

Communication dated Jan. 18, 2018, issued by the Korean Patent Office in counterpart Korean application No. 10-2016-0153317.

(Continued)

*Primary Examiner* — Rochelle D Turchen
(74) *Attorney, Agent, or Firm* — Sughrue Mion, PLLC

(57) ABSTRACT

A method of controlling an ultrasound imaging apparatus includes setting a region of interest on a contrast-enhanced image or an ultrasound image that is registered and displayed; obtaining feature information of the contrast-enhanced image or the ultrasound image from the set region of interest; detecting at least one region, in which feature information similar to the feature information of the region of interest is obtained; and displaying the at least one region that is detected.

14 Claims, 12 Drawing Sheets

(56) References Cited

U.S. PATENT DOCUMENTS

| | | | |
|---|---|---|---|
| 2013/0090557 A1* | 4/2013 | Takagi | A61B 8/481 600/431 |
| 2013/0169782 A1* | 7/2013 | Choi | A61B 5/0077 348/77 |
| 2014/0330107 A1 | 11/2014 | Shin et al. | |
| 2015/0148676 A1 | 5/2015 | Choi et al. | |
| 2015/0213613 A1* | 7/2015 | Prevost | G06T 7/149 382/131 |
| 2015/0297172 A1* | 10/2015 | Takagi | G06K 9/4661 600/443 |

FOREIGN PATENT DOCUMENTS

| | | |
|---|---|---|
| CN | 105722463 A | 6/2016 |
| JP | 2011-245189 A | 12/2011 |
| KR | 10-1024857 B1 | 3/2011 |
| KR | 10-2012-0095730 A | 8/2012 |
| KR | 10-2014-0130888 A | 11/2014 |
| WO | 2006/057740 A2 | 6/2006 |
| WO | 2010/055426 A1 | 5/2010 |

OTHER PUBLICATIONS

Communication dated Apr. 9, 2020, from the State Intellectual Property Office of People's Republic of China in counterpart Application No. 201711147144.X.

Communication dated Feb. 1, 2021 by the National Intellectual Property Administration, PRC in corresponding Chinese Application No. 201711147144.X.

Communication dated Jun. 17, 2021 issued by the Intellectual Property Office of the P.R.China in application No. 201711147144.X.

* cited by examiner

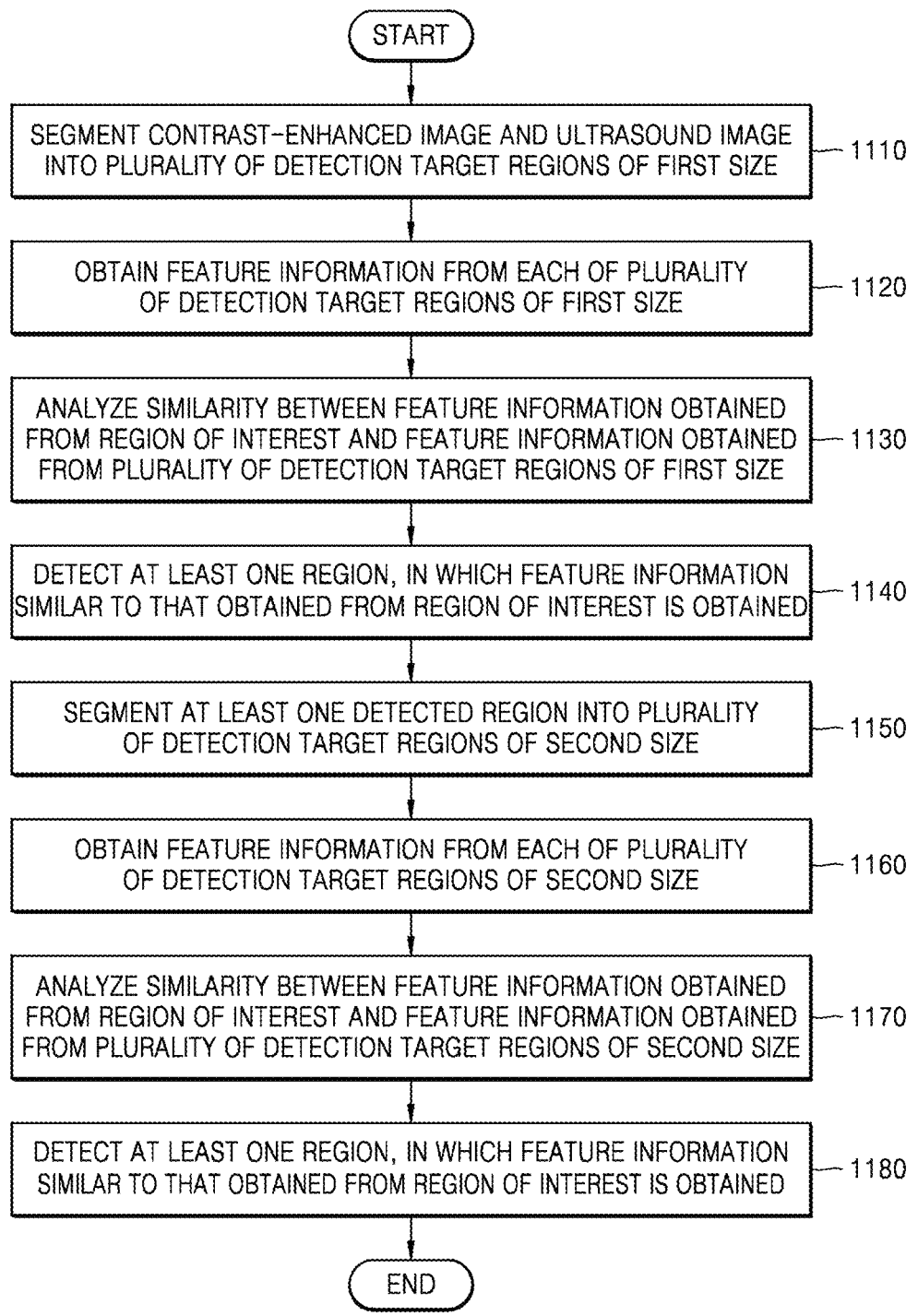

ULTRASOUND IMAGING APPARATUS AND METHOD OF CONTROLLING THE SAME

CROSS-REFERENCE TO RELATED APPLICATION

This application claims the benefit of Korean Patent Application No. 10-2016-0153317, filed on Nov. 17, 2016, in the Korean Intellectual Property Office, the disclosure of which is incorporated herein in its entirety by reference.

BACKGROUND

1. Field

The present disclosure relates to ultrasound imaging apparatuses and methods of controlling the same.

2. Description of the Related Art

Ultrasound diagnostic apparatuses transmit ultrasound signals generated by transducers of a probe to an object and detect information about signals reflected from the object, thereby obtaining at least one image of an internal part of the object, for example, soft tissue or blood flow.

An ultrasound imaging apparatus generates and displays an amplitude (A) mode image, a bright (B) mode image, a motion (M) mode image, a color doppler mode image, and a real-time three-dimensional (3D) ultrasound image.

Also, in a case where it is difficult to find blood vessels or lesions, an ultrasound imaging apparatus generates and displays a contrast-enhanced image by using a signal transmitted from an object to which a contrast agent is injected.

However, in the ultrasound imaging apparatus according to the related art, a user has to set a certain region in an image as a region of interest and identify whether there is a lesion. In particular, if there are a plurality of lesions in the image, the user has to identify each one of the plurality of lesions individually. Moreover, some users are not capable of identifying whether there is a lesion.

SUMMARY

Provided are ultrasound imaging apparatuses and methods of controlling the ultrasound imaging apparatuses capable of detecting a region having features similar to those of a region of interest set in a contrast-enhanced image and an ultrasound image that are registered.

Provided are non-transitory computer-readable recording media having recorded thereon a program, which when executed by a computer, performs the above methods.

Additional aspects will be set forth in part in the description which follows and, in part, will be apparent from the description, or may be learned by practice of the presented embodiments.

According to an aspect of an embodiment, a method of controlling an ultrasound imaging apparatus includes: setting a region of interest on a contrast-enhanced image or an ultrasound image that is registered and displayed; obtaining feature information of the contrast-enhanced image or the ultrasound image from the set region of interest; detecting at least one region, in which feature information similar to the feature information of the region of interest is obtained; and displaying the at least one region that is detected.

According to an aspect of another embodiment, there is provided a non-transitory computer-readable recording medium having embodied thereon a program for executing the above method.

According to an aspect of another embodiment, an ultrasound imaging apparatus includes: at least one processor configured to generate a contrast-enhanced image and an ultrasound image of an object by using a signal received through a probe, and to register the contrast-enhanced image and the ultrasound image; a display configured to display the contrast-enhanced image and the ultrasound image that are registered; and an input interface configured to receive a signal for setting a region of interest in the contrast-enhanced image or the ultrasound image, wherein the at least one processor is configured to set the region of interest in the contrast-enhanced image and the ultrasound image by using the signal, to obtain feature information of the contrast-enhanced image and the ultrasound image from the set region of interest, and to detect at least one region, in which feature information similar to the feature information obtained from the region of interest is obtained, wherein the display is configured to display at least one detected region.

According to an aspect of another embodiment, a method of controlling an ultrasound imaging apparatus includes: setting a region of interest in a contrast-enhanced image or in an ultrasound image that is registered and displayed; obtaining feature information of the set region of interest of the contrast-enhanced image or the ultrasound image; detecting at least one region of the contrast-enhanced image or the ultrasound image, in which feature information similar to the feature information of the set region of interest is obtained, the at least one region being different from the set region of interest; and displaying the at least one region that is detected.

According to an aspect of another embodiment, an ultrasound imaging apparatus includes: at least one processor configured to generate a contrast-enhanced image and an ultrasound image of an object by using a signal received through a probe, and to register the contrast-enhanced image and the ultrasound image; a display configured to display the contrast-enhanced image and the ultrasound image that are registered; and an input interface configured to receive a signal for setting a region of interest in the contrast-enhanced image or in the ultrasound image, wherein the at least one processor is configured to set the region of interest in the contrast-enhanced image and the ultrasound image by using the signal, to obtain feature information of the set region of interest of the contrast-enhanced image and the ultrasound image, and to detect at least one region of the contrast-enhanced image or the ultrasound image, in which feature information similar to the feature information obtained from the set region of interest is obtained, the at least one region being different from the set region of interest, wherein the display is configured to display at least one region.

BRIEF DESCRIPTION OF THE DRAWINGS

These and/or other aspects will become apparent and more readily appreciated from the following description of the embodiments, taken in conjunction with the accompanying drawings in which:

FIG. 11 is a flowchart illustrating a method of controlling an ultrasound imaging apparatus according to an embodiment of the present disclosure;

DETAILED DESCRIPTION

Figure 1:
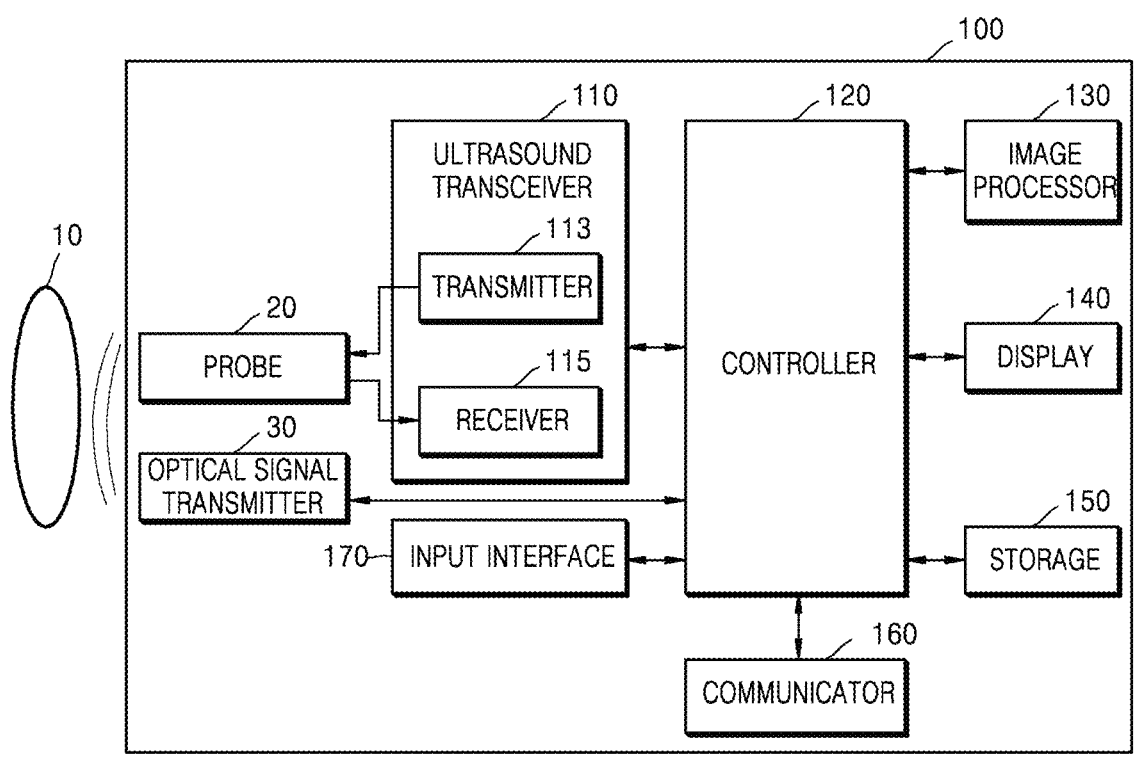
FIG. 1 is a block diagram illustrating an ultrasound diagnosis apparatus according to an exemplary embodiment.

The present specification describes principles of the present disclosure and provides embodiments so that a scope of the present disclosure may be clarified and one of ordinary skill in the art would carry out the present disclosure. The embodiments may be implemented in various types. Expressions such as "at least one of," when preceding a list of elements, modify the entire list of elements and do not modify the individual elements of the list.

In the following description, the same drawing reference numerals are used for the same elements even in different drawings. The matters defined in the description, such as detailed construction and elements, are provided to assist in a comprehensive understanding of exemplary embodiments. Thus, it is apparent that exemplary embodiments can be carried out without those specifically defined matters. Also, well-known functions or constructions are not described in detail since they would obscure exemplary embodiments with unnecessary detail.

Terms such as "part" and "portion" used herein denote those that may be embodied by software or hardware. According to exemplary embodiments, a plurality of parts or portions may be embodied by a single unit or element, or a single part or portion may include a plurality of elements.

In exemplary embodiments, an image may include any medical image acquired by various medical imaging apparatuses such as a magnetic resonance imaging (MRI) apparatus, a computed tomography (CT) apparatus, an ultrasound imaging apparatus, or an X-ray apparatus.

Also, in the present specification, an "object", which is a thing to be imaged, may include a human, an animal, or a part thereof. For example, an object may include a part of a human, that is, an organ or a tissue, or a phantom.

Throughout the specification, an ultrasound image refers to an image of an object processed based on ultrasound signals transmitted to the object and reflected therefrom.

Throughout the specification, "feature information" refers to information regarding features of a region obtained from the region that is a part of an ultrasound image and a contrast-enhanced image. For example, the feature information may include image signal data, parameters obtained from an image signal, and a vector value of an image signal.

Certain exemplary embodiments are described in greater detail below with reference to the accompanying drawings.

FIG. 1 is a block diagram illustrating a configuration of an ultrasound diagnosis apparatus 100, i.e., a diagnostic apparatus, according to an exemplary embodiment.

Referring to FIG. 1, the ultrasound diagnosis apparatus 100 may include a probe 20, an ultrasound transceiver 110, a controller 120, an image processor 130, one or more displays 140, a storage 150, e.g., a memory, a communicator 160, i.e., a communication device or an interface, and an input interface 170.

The ultrasound diagnosis apparatus 100 may be of a cart-type or a portable-type ultrasound diagnosis apparatus, that is portable, moveable, mobile, or hand-held. Examples of the portable-type ultrasound diagnosis apparatus 100 may include a smart phone, a laptop computer, a personal digital assistant (PDA), and a tablet personal computer (PC), each of which may include a probe and a software application, but embodiments are not limited thereto.

The probe 20 may include a plurality of transducers. The plurality of transducers may transmit ultrasound signals to an object 10 in response to transmitting signals received by the probe 20, from a transmitter 113. The plurality of transducers may receive ultrasound signals reflected from the object 10 to generate reception signals. In addition, the probe 20 and the ultrasound diagnosis apparatus 100 may be formed in one body (e.g., disposed in a single housing), or the probe 20 and the ultrasound diagnosis apparatus 100 may be formed separately (e.g., disposed separately in separate housings) but linked wirelessly or via wires. In addition, the ultrasound diagnosis apparatus 100 may include one or more probes 20 according to embodiments.

The probe 20 may generate a contrast-enhanced signal including various contrast patterns that are shown when a microbubble ultrasonography contrast injected into the object 10 is dispersed to blood vessels and organs of the object.

The controller 120 may control the transmitter 113 to generate transmitting signals to be applied to each of the plurality of transducers based on a position and a focal point of the plurality of transducers included in the probe 20.

The controller 120 may control the ultrasound receiver 115 to generate ultrasound data by converting reception signals received from the probe 20 from analogue to digital signals and summing the converted reception signals, based on a position and a focal point of the plurality of transducers.

The image processor 130 may generate an ultrasound image by using ultrasound data generated from the ultrasound receiver 115.

The image processor 130 may generate a contrast-enhanced image by using the contrast-enhanced signal generated by the ultrasound receiver 115. The image processor 130 may simultaneously generate an ultrasound image and a contrast-enhanced image in real-time.

The controller 120 and the image processor 130 may be implemented as one processor, or may be each implemented as one or more processors. The processor may be implemented as an array of a plurality of logic gates, or as a combination of a universal microprocessor and a memory storing programs that may be executed in the microprocessor. In addition, one of ordinary skill in the art would appreciate that the central processor may be implemented as other types of hardware.

The display 140 may display a generated ultrasound image, the contrast-enhanced image and various pieces of information processed by the ultrasound diagnosis apparatus 100. The ultrasound diagnosis apparatus 100 may include two or more displays 140 according to the present exemplary embodiment. The display 140 may include a touch screen in combination with a touch panel.

The controller 120 may control the operations of the ultrasound diagnosis apparatus 100 and flow of signals between the internal elements of the ultrasound diagnosis apparatus 100. The controller 120 may include a memory for storing a program or data to perform functions of the ultrasound diagnosis apparatus 100 and a processor and/or a microprocessor (not shown) for processing the program or data. For example, the controller 120 may control the operation of the ultrasound diagnosis apparatus 100 by receiving a control signal from the input interface 170 or an external apparatus.

The ultrasound diagnosis apparatus 100 may include the communicator 160 and may be connected to external apparatuses, for example, servers, medical apparatuses, and portable devices such as smart phones, tablet personal computers (PCs), wearable devices, etc., via the communicator 160.

The communicator 160 may include at least one element capable of communicating with the external apparatuses. For example, the communicator 160 may include at least one among a short-range communication module, a wired communication module, and a wireless communication module.

The communicator 160 may receive a control signal and data from an external apparatus and transmit the received control signal to the controller 120 so that the controller 120 may control the ultrasound diagnosis apparatus 100 in response to the received control signal.

The controller 120 may transmit a control signal to the external apparatus via the communicator 160 so that the external apparatus may be controlled in response to the control signal of the controller 120.

For example, the external apparatus connected to the ultrasound diagnosis apparatus 100 may process the data of the external apparatus in response to the control signal of the controller 120 received via the communicator 160.

A program for controlling the ultrasound diagnosis apparatus 100 may be installed in the external apparatus. The program may include command languages to perform part of operation of the controller 120 or the entire operation of the controller 120.

The program may be pre-installed in the external apparatus or may be installed by a user of the external apparatus by downloading the program from a server that provides applications. The server that provides applications may include a recording medium where the program is stored.

The storage 150 may store various data or programs for driving and controlling the ultrasound diagnosis apparatus 100, input and/or output ultrasound data, ultrasound images, applications, etc.

The storage 150 may store feature information of a region of interest set on the contrast-enhanced image and the ultrasound image. The storage 150 may store feature information obtained from a region included in the contrast-enhanced image and the ultrasound image. The storage 150 may store a result of analyzing similarity between feature information obtained from the region included in the contrast-enhanced image and the ultrasound image and feature information of the region of interest set on the contrast-enhanced image and the ultrasound image.

The input interface 170 may receive a user's input to control the ultrasound diagnosis apparatus 100 and may include a keyboard, button, keypad, mouse, trackball, jog switch, knob, a touchpad, a touch screen, a microphone, a motion input means, a biometrics input means, etc. For example, the user's input may include inputs for manipulating buttons, keypads, mice, trackballs, jog switches, or knobs, inputs for touching a touchpad or a touch screen, a voice input, a motion input, and a bioinformation input, for example, iris recognition or fingerprint recognition, but an exemplary embodiment is not limited thereto.

The input interface 170 may receive a user input for setting the region of interest.

An example of the ultrasound diagnosis apparatus 100 according to the present exemplary embodiment is described below with reference to FIGS. 2A, 2B, and 2C.

Figure 2C:
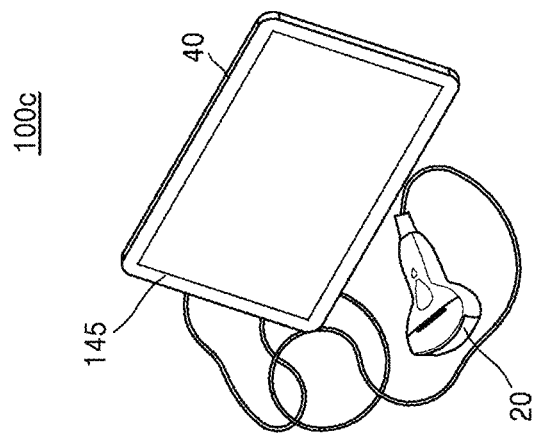
FIGS. 2A, 2B, and 2C are diagrams respectively illustrating an ultrasound diagnosis apparatus according to an exemplary embodiment.
Figure 2B:
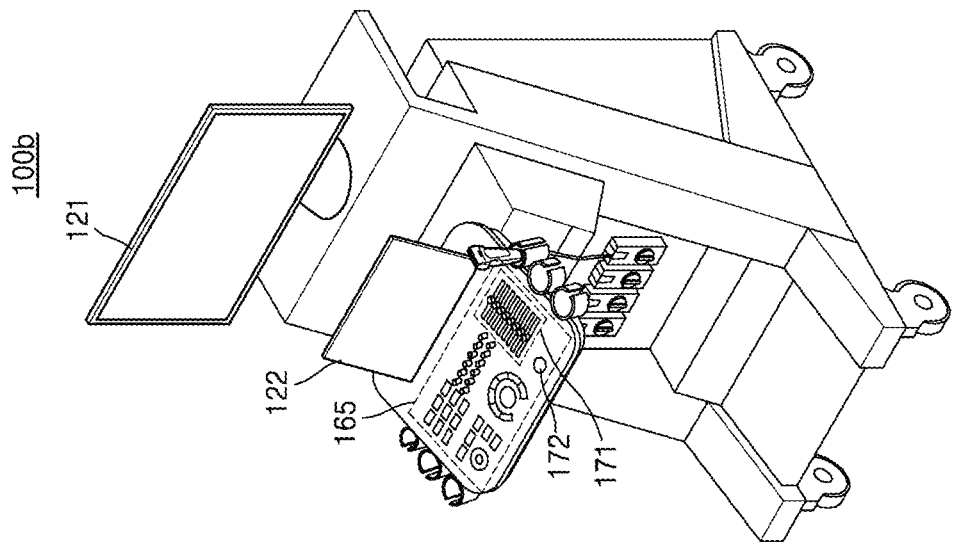
Figure 2A:
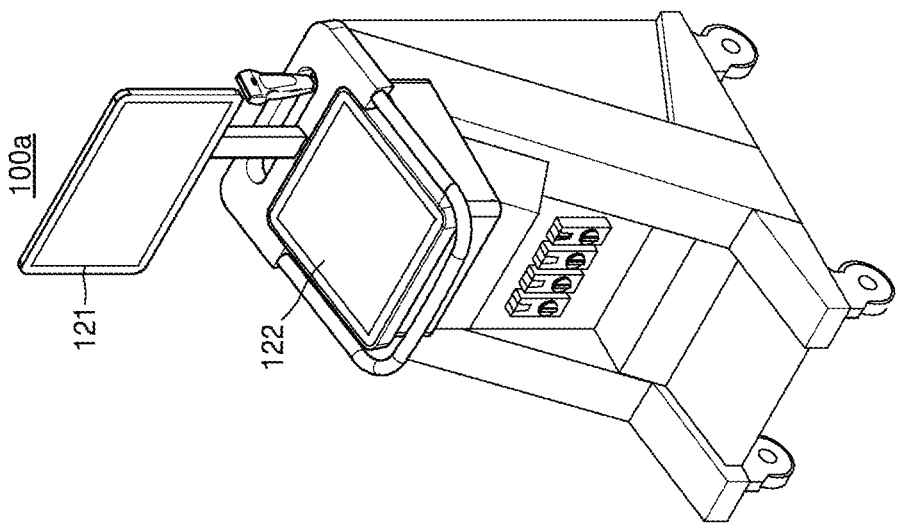

FIGS. 2A, 2B, and 2C are diagrams illustrating ultrasound diagnosis apparatus according to an exemplary embodiment.

Referring to FIGS. 2A and 2B, the ultrasound diagnosis apparatus 100 may include a main display 121 and a sub-display 122. At least one among the main display 121 and the sub-display 122 may include a touch screen. The main display 121 and the sub-display 122 may display ultrasound images and/or various information processed by the ultrasound diagnosis apparatus 100. The main display 121 and the sub-display 122 may provide graphical user interfaces (GUI), thereby receiving user's inputs of data to control the ultrasound diagnosis apparatus 100. For example, the main display 121 may display an ultrasound image and the sub-display 122 may display, as a GUI, a control panel to control display of the ultrasound image. The sub-display 122 may receive an input of data to control the display of an image through the control panel displayed as a GUI. The ultrasound diagnosis apparatus 100 may control the display of the ultrasound image on the main display 121 by using the input control data.

Referring to FIG. 2B, the ultrasound diagnosis apparatus 100 may include a control panel 165. The control panel 165 may include buttons, trackballs, jog switches, or knobs, and may receive data to control the ultrasound diagnosis apparatus 100 from the user. For example, the control panel 165 may include a time gain compensation (TGC) button 171 and a freeze button 172. The TGC button 171 is to set a TGC value for each depth of an ultrasound image. Also, when an input of the freeze button 172 is detected during scanning an ultrasound image, the ultrasound diagnosis apparatus 100 may keep displaying a single frame image at that time point.

The buttons, trackballs, jog switches, and knobs included in the control panel 165 may be provided as a GUI to the main display 121 or the sub-display 122.

Referring to FIG. 2C, the ultrasound diagnosis apparatus 100 may include a portable device. An example of the portable ultrasound diagnosis apparatus 100 may include, for example, smart phones including probes and applications, laptop computers, personal digital assistants (PDAs), or tablet PCs, but an exemplary embodiment is not limited thereto.

The ultrasound diagnosis apparatus 100 may include the probe 20 and a main body 40. The probe 20 may be connected to one side of the main body 40 by wire or wirelessly. The main body 40 may include a touch screen 145. The touch screen 145 may display an ultrasound image, various pieces of information processed by the ultrasound diagnosis apparatus 100, and/or a GUI.

Figure 3:
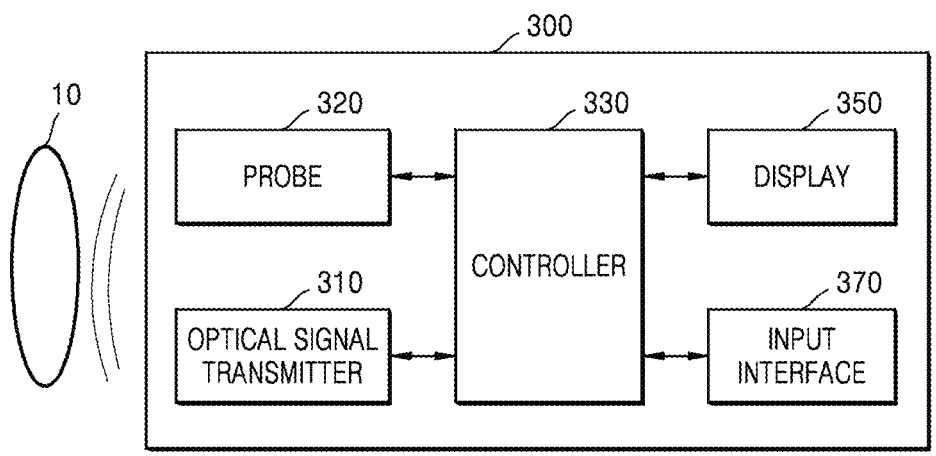
FIG. 3 is a block diagram of an ultrasound imaging apparatus according to an embodiment of the present disclosure.

FIG. 3 is a block diagram of an ultrasound imaging apparatus 300 according to an embodiment of the present disclosure.

According to an embodiment illustrated in FIG. 3, the ultrasound imaging apparatus 300 may include a probe 320, a controller 330, a display 350, and an input interface 370.

The probe 320 may include a plurality of transducers. The plurality of transducers may transmit ultrasound signals to the object 10. The plurality of transducers receive ultrasound signals reflected by the object 10 or a contrast-enhanced signal generated from the contrast agent injected into the object 10, and generate reception signals.

The controller 330 may include at least one processor. The controller 330 may control each of the components included in the ultrasound imaging apparatus 300. The controller 330 may generate an ultrasound signal by using the received ultrasound signal. The controller 330 may generate a contrast-enhanced image by using the received contrast-enhanced signal. The controller 330 may simultaneously generate the ultrasound image and the contrast-enhanced image.

According to the embodiment, the controller 330 may control the probe 320 to generate ultrasound data or contrast-enhanced data by performing analog-digital conversion of the signal transmitted from the probe 320 and combining the digitally converted signals based on locations of the plurality of transducers and focusing points.

According to the embodiment, the controller 330 may set a region of interest based on the user input received through the input interface 370.

According to the embodiment, the controller 330 may obtain feature information of the contrast-enhanced image. For example, the controller 330 may generate a time intensity curve representing a variation in an intensity of the received contrast-enhanced signal by using the received contrast-enhanced signal. The controller 330 may obtain feature information of the contrast-enhanced image by using the generated time intensity curve.

According to the embodiment, the controller 330 may obtain feature information of the ultrasound image. For example, the controller 330 may obtain the feature information of the ultrasound signal by using an intensity of an ultrasound image signal.

According to the embodiment, the controller 330 may obtain features of the contrast-enhanced image and feature information of the ultrasound image. For example, the controller 330 may obtain the feature information based on the time intensity curve representing the variation in the intensity of the contrast-enhanced signal and the intensity of the ultrasound image signal. The controller 330 may obtain the feature information based on a plurality of parameters that may be obtained from the time intensity curve representing the variation in the intensity of the contrast-enhanced signal and a plurality of parameters that may be obtained from the intensity of the ultrasound image signal.

According to the embodiment, the controller 330 may segment the contrast-enhanced image and the ultrasound image into a plurality of detection target regions having a first size. For example, the controller 330 may segment the contrast-enhanced image and the ultrasound image into the detection target regions having the first size that is equal to a size of the region of interest. The controller 330 may segment the contrast-enhanced image and the ultrasound image so that the plurality of detection target regions having the first size may overlap with one another. The controller 330 may segment the contrast-enhanced image and the ultrasound image so that the plurality of detection target regions having the first size may overlap with one another by an area smaller than the first size.

According to the embodiment, the controller 330 may obtain feature information from each of the plurality of detection target regions having the first size. For example, the controller 330 may obtain feature information from each of the plurality of detection target regions of the first size segmented from the contrast-enhanced image. The controller 330 may obtain feature information from each of the plurality of detection target regions of the first size segmented from the ultrasound image. The controller 330 may obtain feature information of each of the contrast-enhanced image and the ultrasound image that are registered, wherein the contrast-enhanced image and the ultrasound image are segmented into the plurality of detection target regions of the first size.

The controller 330 may obtain the feature information based on a plurality of parameters that may be obtained from the time intensity curve of the contrast-enhanced signal transmitted from each of the plurality of detection target regions of the first size segmented from the contrast-enhanced image. The controller 330 may obtain the feature information based on a plurality of parameters that may be obtained from the intensity of the ultrasound image signal transmitted from each of the plurality of detection target regions of the first size segmented from the ultrasound image. The controller 330 may obtain the feature information based on the plurality of parameters that may be obtained from the contrast-enhanced image and the ultrasound image that are segmented into the plurality of detection target regions of the first size.

According to the embodiment, the controller 330 may analyze similarity between the feature information obtained from the region of interest and the feature information obtained from the contrast-enhanced image and the ultrasound image segmented into the plurality of detection target regions of the first size. The controller 330 may analyze the similarity by comparing a difference value between a first parameter included in the feature information obtained from the region of interest and a plurality of second parameters included in the feature information obtained from the plurality of detection target regions of the first size with a threshold value set in advance.

According to the embodiment, the controller 330 may detect a region, in which feature information similar to that of the region of interest is obtained, by using an analysis result of the similarity between the feature information obtained from the region of interest and the feature information obtained from the plurality of detection target regions of the first size.

According to the embodiment, the controller 330 may segment the region, in which the feature information similar to that of the region of interest is detected, into a plurality of detection target regions having a second size. The controller 330 may segment the region, in which the feature information similar to that of the region of interest is detected, into the detection target regions of the second size that is smaller than the first size. The controller 330 may segment the region, in which the feature information similar to that of the region of interest is obtained, into the detection target regions of the second size to overlap with one another. The controller 330 may segment the region, in which the feature information similar to that of the region of interest, into the detection target regions of the second size to overlap with one another by an area smaller than the second size.

According to the embodiment, the controller 330 may analyze similarity between the feature information obtained from the region of interest and feature information obtained from the plurality of detection target regions of the second size. The controller 330 may analyze the similarity by comparing a difference value between a first parameter included in the feature information obtained from the region of interest and a plurality of second parameters included in the feature information obtained from the plurality of detection target regions of the second size with a threshold value set in advance.

According to the embodiment, the controller 330 may perform a color-coding on at least one region, in which feature information similar to that of the region of interest is obtained, in at least one of the contrast-enhanced image and the ultrasound image.

According to the embodiment, the controller 330 may perform the color-coding on at least one region, in which the feature information similar to that of the region of interest is obtained, into a preset color corresponding to the similarity of the feature information obtained from the region of interest.

According to the embodiment, the display 350 may display the region, in which the feature information similar to that of the detected region of interest is obtained. For example, the display 350 may display the color-coded region. The display 350 may display the region that is color-coded into the preset color corresponding to the similarity of the feature information obtained from the region of interest. The display 350 may display a contour line of the region, in which the feature information similar to that of the detected region of interest is obtained.

The input interface 370 may receive a user input for setting the region of interest.

Figure 4:
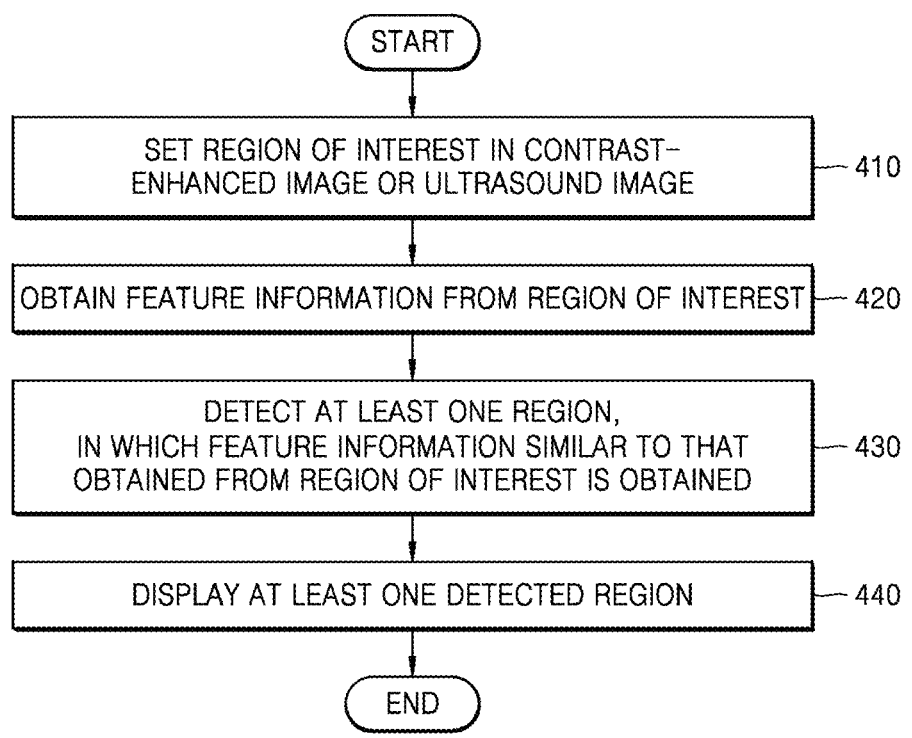
FIG. 4 is a flowchart illustrating a method of controlling an ultrasound imaging apparatus according to an embodiment of the present disclosure.
Figure 5:
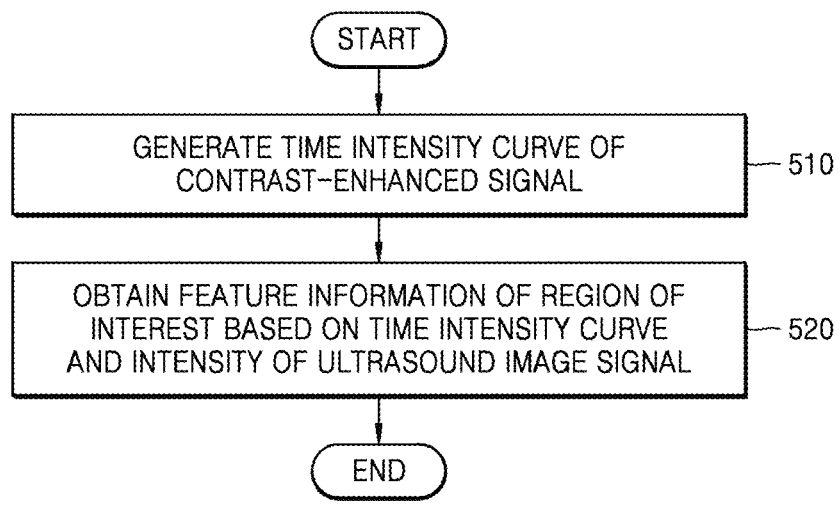
FIG. 5 is a flowchart illustrating a method of controlling an ultrasound imaging apparatus according to an embodiment of the present disclosure.

In addition, FIGS. 4 and 5 are flowcharts illustrating methods of controlling an ultrasound imaging apparatus according to an embodiment of the present disclosure.

According to the embodiment illustrated with reference to FIG. 4, the method of controlling the ultrasound imaging apparatus may include setting a region of interest in a contrast-enhanced image or an ultrasound image (410), obtaining feature information of the contrast-enhanced image and the ultrasound image from the set region of interest (420), detecting at least one region, in which feature information similar to that of the region of interest is obtained (430), and displaying the detected at least one region (440).

In operation 410, the ultrasound imaging apparatus 300 may set a region of interest in a contrast-enhanced image or an ultrasound image.

The ultrasound imaging apparatus 300 may receive a contrast-enhanced signal from a contrast agent injected into the object 10.

The ultrasound imaging apparatus 300 may receive an ultrasound signal from the object 10.

The ultrasound imaging apparatus 300 may generate a contrast-enhanced image by using the received contrast-enhanced signal and generate an ultrasound image by using the received ultrasound signal.

The ultrasound imaging apparatus 300 may register the contrast-enhanced image and the ultrasound image with each other.

The ultrasound imaging apparatus 300 may display the registered contrast-enhanced image and the ultrasound image.

The ultrasound imaging apparatus 300 may receive a user input for setting a region of interest in the contrast-enhanced image or the ultrasound image that are registered and displayed. The ultrasound imaging apparatus 300 may set the region of interest on at least one of the contrast-enhanced image and the ultrasound image based on the user input. For example, when the ultrasound imaging apparatus 300 receives an input for setting a region of interest on the contrast-enhanced image from the user, the ultrasound imaging apparatus 300 may set the region of interest on the contrast-enhanced image based on the input from the user.

When the ultrasound imaging apparatus 300 receives an input for setting a region of interest on the ultrasound image from the user, the ultrasound imaging apparatus 300 may set the region of interest on the ultrasound image based on the input from the user.

When the ultrasound imaging apparatus 300 receives an input for setting a region of interest on the contrast-enhanced image or the ultrasound image from the user, the ultrasound imaging apparatus 300 may set the region of interest on each of the contrast-enhanced image and the ultrasound image based on the input from the user.

When the ultrasound imaging apparatus 300 receives an input for setting a region of interest on the contrast-enhanced image registered to the ultrasound image from the user, the ultrasound imaging apparatus 300 may set the region of interest on the contrast-enhanced image and the ultrasound image that are registered, based on the input from the user.

When the ultrasound imaging apparatus 300 receives an input for setting a region of interest on the ultrasound image registered to the contrast-enhanced image from the user, the ultrasound imaging apparatus 300 may set the region of interest on the contrast-enhanced image and the ultrasound image that are registered, based on the input from the user.

In addition, in operation 420, the ultrasound imaging apparatus 300 may obtain feature information of the contrast-enhanced image and the ultrasound image from the set region of interest.

According to the embodiment, the ultrasound imaging apparatus 300 may obtain the feature information of the contrast-enhanced image. For example, the ultrasound imaging apparatus 300 may generate a time intensity curve representing a variation in the intensity of the contrast-enhanced signal by using the received contrast-enhanced signal. The ultrasound imaging apparatus 300 may obtain the feature information of the contrast-enhanced image by using the generated time intensity curve. The ultrasound imaging apparatus 300 may obtain the feature information of the contrast-enhanced image by using a parameter that may be obtained from the generated time intensity curve.

According to the embodiment, the ultrasound imaging apparatus 300 may obtain the feature information of the ultrasound image. For example, the ultrasound imaging apparatus 300 may obtain the feature information of the ultrasound signal by using an intensity of an ultrasound image signal. The ultrasound imaging apparatus 300 may obtain the feature information of the ultrasound image by using a parameter that may be obtained from the ultrasound image.

According to the embodiment, the ultrasound imaging apparatus 300 may obtain the feature information of the contrast-enhanced image and the ultrasound image. For example, the ultrasound imaging apparatus 300 may obtain the feature information based on the time intensity curve representing the variation in the intensity of the contrast-enhanced signal and the intensity of the ultrasound image signal. The ultrasound imaging apparatus 300 may obtain the feature information based on the parameter that may be obtained from the time intensity curve representing the variation in the intensity of the contrast-enhanced signal and the parameter that may be obtained from the ultrasound image.

The embodiment of operation 420 will be additionally described later with reference to FIGS. 5, 6, and 8A to 8C.

In addition, in operation 430, the ultrasound imaging apparatus 300 may detect at least one region, in which feature information similar to that of the region of interest is obtained.

According to the embodiment, the ultrasound imaging apparatus 300 may detect at least one region, in which the feature information similar to that of the region of interest is obtained, by analyzing similarity between the feature information obtained from a part of the contrast-enhanced image and the feature information obtained from the region of interest.

According to the embodiment, the ultrasound imaging apparatus 300 may detect at least one region, in which the feature information similar to that of the region of interest is obtained, by analyzing similarity between the feature information obtained from a part of the ultrasound image and the feature information obtained from the region of interest.

According to the embodiment, the ultrasound imaging apparatus 300 may detect at least one region, in which the feature information similar to that of the region of interest is obtained, by analyzing similarity between the feature information obtained from a part of the contrast-enhanced image and the ultrasound image and the feature information obtained from the region of interest.

According to the embodiment, the ultrasound imaging apparatus 300 may segment the contrast-enhanced image and the ultrasound image into a plurality of detection target regions, and may detect at least one region, in which the feature information similar to that of the region of interest is obtained.

Operation 430 according to the embodiment will be additionally described later with reference to FIGS. 7A and 7B, and 9 to 13.

In addition, in operation 440, the ultrasound imaging apparatus 300 may display at least one detected region, in which feature information similar to that of the region of interest is obtained.

According to the embodiment, the ultrasound imaging apparatus 300 may color-code and display the at least one detected region, in which the feature information similar to that of the region of interest is obtained.

Operation 440 according to the embodiment will be additionally described later with reference to FIGS. 14 and 15.

Figure 6:
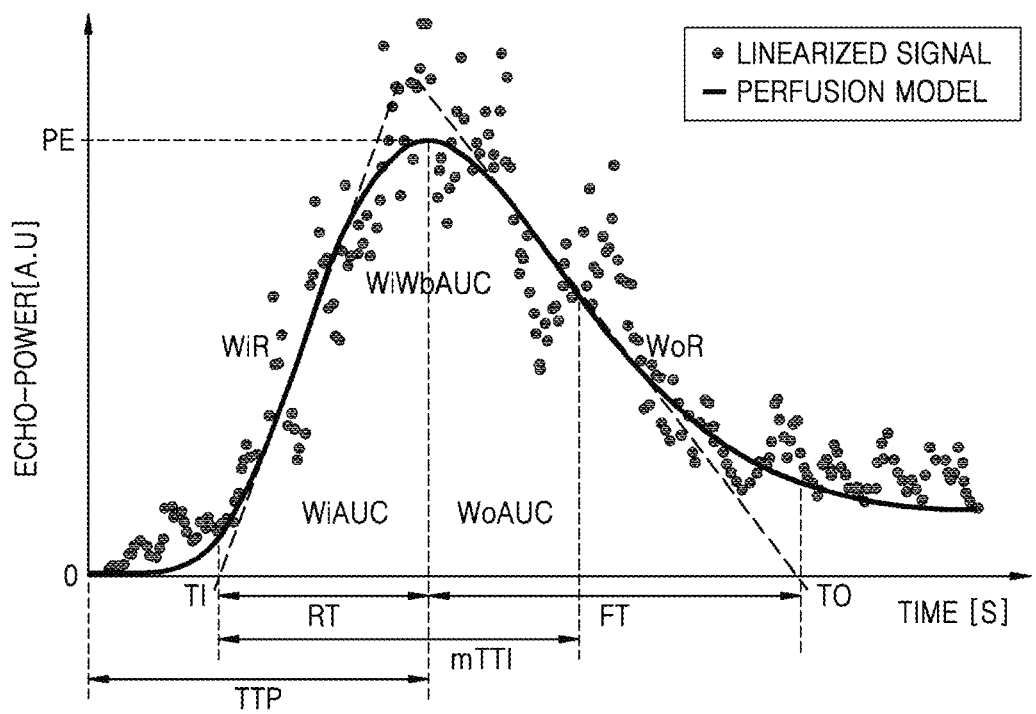
FIG. 6 is a diagram of a time-intensity curve of a contrast-enhanced signal of an object according to an embodiment of the present disclosure.
Figure 8A:
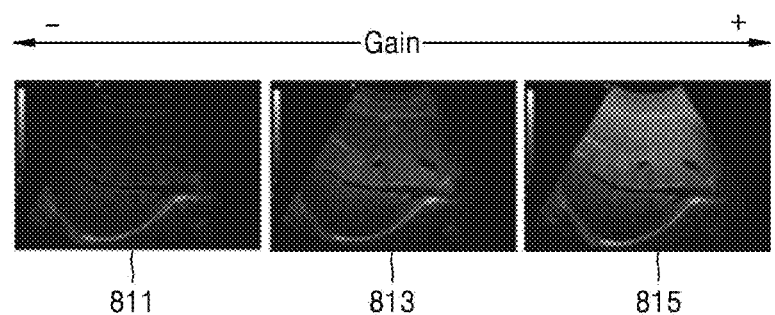
FIG. 8A is a diagram illustrating feature information obtained from an ultrasound image according to an embodiment of the present disclosure.
Figure 8B:
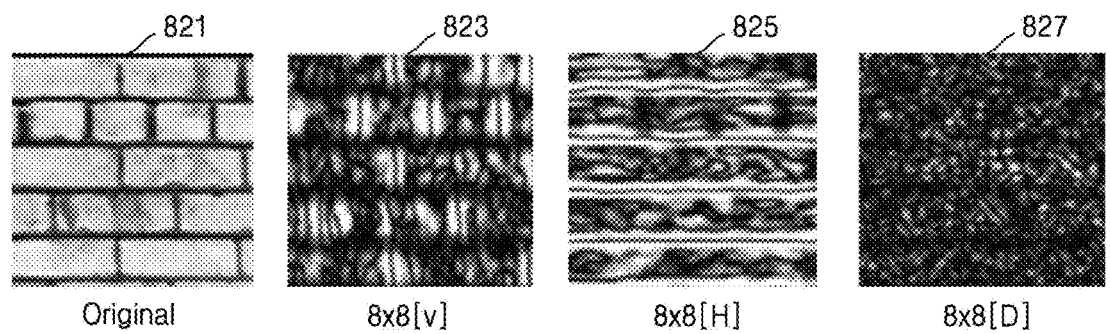
FIG. 8B is a diagram illustrating feature information obtained from an ultrasound image according to an embodiment of the present disclosure.
Figure 8C:
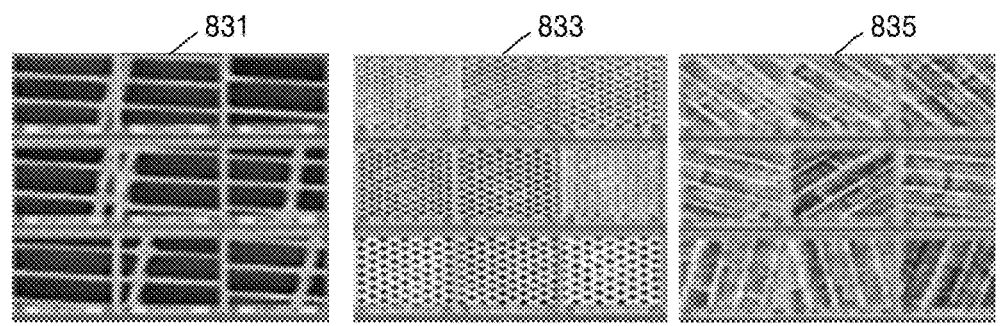
FIG. 8C is a diagram illustrating feature information obtained from an ultrasound image according to an embodiment of the present disclosure.

In addition, FIG. 5 is a flowchart illustrating a method of controlling an ultrasound imaging apparatus according to the embodiment illustrated in operation 420, FIG. 6 is a diagram of a time intensity curve of the contrast-enhanced signal of an object according to an embodiment of the present disclosure, and FIGS. 8A to 8C are diagrams of feature information obtained from an ultrasound image according to an embodiment of the present disclosure.

According to the embodiment illustrated with reference to FIG. 5, the process of obtaining the feature information of the contrast-enhanced image and the ultrasound image from the set region of interest by the ultrasound imaging apparatus 300 may include generating a time intensity curve of the contrast-enhanced signal (510), and obtaining the feature information of the region of interest based on the time intensity curve of the contrast-enhanced signal and the intensity of the ultrasound image signal (520).

In operation 510, the ultrasound imaging apparatus 300 may generate the time intensity curve of the contrast-enhanced signal. The ultrasound imaging apparatus 300 may generate the time intensity curve of the contrast-enhanced signal transmitted from the set region of interest. The ultrasound imaging apparatus 300 may generate the time intensity curve of the contrast-enhanced signal transmitted from each of the plurality of detection target regions of the first size segmented from the contrast-enhanced image. The ultrasound imaging apparatus 300 may generate a time intensity curve of a contrast-enhanced signal transmitted from each of a plurality of detection target regions of the second size, which are segmented from the plurality of detection target regions of the first size.

In operation 520, the ultrasound imaging apparatus 300 may obtain the feature information of the region of interest based on the generated time intensity curve of the contrast-enhanced signal and the intensity of the ultrasound image signal.

According to the embodiment, the ultrasound imaging apparatus 300 may obtain the feature information of the region of interest by using a parameter obtained from the time intensity curve of the contrast-enhanced signal of FIG. 6. The parameter obtained from the time intensity curve of the contrast-enhanced signal shown in FIG. 6 may be a parameter in Table 1 below. For example, the ultrasound imaging apparatus 300 may obtain the feature information of the region of interest by using the parameter obtained from the time intensity curve of the contrast-enhanced signal, but is not limited thereto.

TABLE 1

| | | |
|---|---|---|
| PE | Peak Enhancement | [a.u] |
| WiAUC | Wash-in Area Under the Curve (AUC (TI:TTP)) | [a.u] |
| RT | Rise Time (TTP-Ti) | [s] |
| mTTl | mean Transit Time local (mTT-Tl) | [s] |
| TTP | Time To Peak | [s] |
| WiR | Wash-in Rate (maximum slope) | [a.u] |
| WiPI | Wash-in Perfusion index (WiAUC/RT) | [a.u] |
| WoAUC | Wash-out AUC(AUC (TTP:TO)) | [a.u] |
| WiWoAUC | Wash-in and Wash-out AUC (WiAUC + WoAUC) | [a.u] |
| FT | Fall Time (TO-TTP) | [s] |
| WoR | Wash-out Rate (minimum slope) | [a.u] |
| QOF | Quality Of Fit between the echo-power signal and f(t) | [%] |

According to the embodiment, the ultrasound imaging apparatus 300 may obtain the feature information of the region of interest by using a parameter regarding the intensity of the ultrasound image signal. For example, the ultrasound imaging apparatus 300 may obtain the feature information of the region of interest by using parameters regarding the intensity of the ultrasound image signal shown in FIGS. 8A to 8C. The ultrasound imaging apparatus 300 may obtain the feature information of the region of interest by using a parameter regarding brightness characteristic of the ultrasound image shown in FIG. 8A (e.g., a mean value). The ultrasound imaging apparatus 300 may obtain the feature information of the region of interest by using a parameter regarding brightness variation of the ultrasound image in a transverse direction, a longitudinal direction, and a diagonal direction shown in FIG. 8B (e.g., a ranklet value). The ultrasound imaging apparatus 300 may obtain the feature information of the region of interest by using a parameter regarding a distribution degree and arrangement of pixels in the ultrasound image shown in FIG. 8C (e.g., a homogeneous texture value).

Figure 7A:
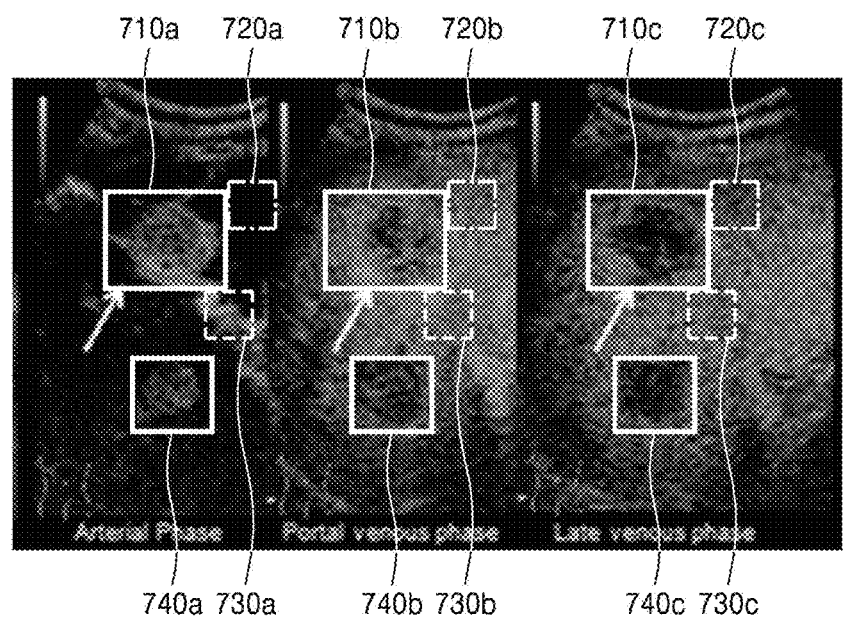
FIGS. 7A and 7B are diagrams of each region in a contrast-enhanced image and a time-intensity curve corresponding to each region, according to an embodiment of the present disclosure.
Figure 7B:
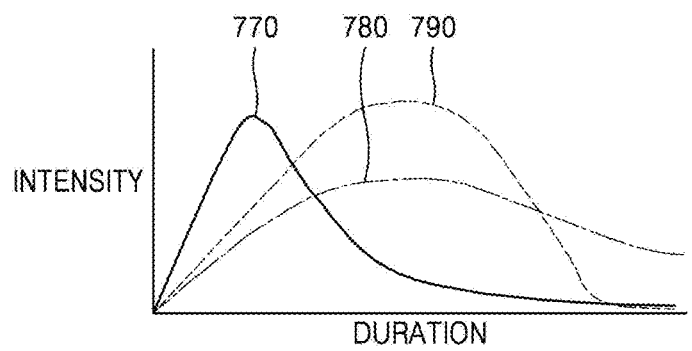

FIGS. 7A and 7B are diagrams showing each region in a contrast-enhanced image according to operation 430 and a time-intensity curve corresponding to each region.

According to the embodiment, the ultrasound imaging apparatus 300 may detect at least one region, in which a time intensity curve of the contrast-enhanced signal similar to that of the contrast-enhanced signal obtained from a part of the contrast-enhanced image is obtained. In detail, the ultrasound imaging apparatus 300 may analyze similarity between a time intensity curve 770 of the contrast-enhanced signal obtained from regions of interest 710a, 710b, and 710c of a contrast-enhanced image of the artery, a contrast-enhanced image of the portal, and a contrast-enhanced image of the vein, and time intensity curves 780 and 790 of the contrast-enhanced signals obtained from parts 720a, 720b, 720c, 730a, 730b, and 730c of the contrast-enhanced image of the artery, the contrast-enhanced image of the portal, and the contrast-enhanced image of the vein. The ultrasound imaging apparatus 300 may detect at least one region 740a, 740b, and 740c in which the time intensity curve of the contrast-enhanced signal similar to the time intensity curve 770 of the contrast-enhanced signal obtained from the regions of interest 710a, 710b, and 710c is obtained.

Figure 9:
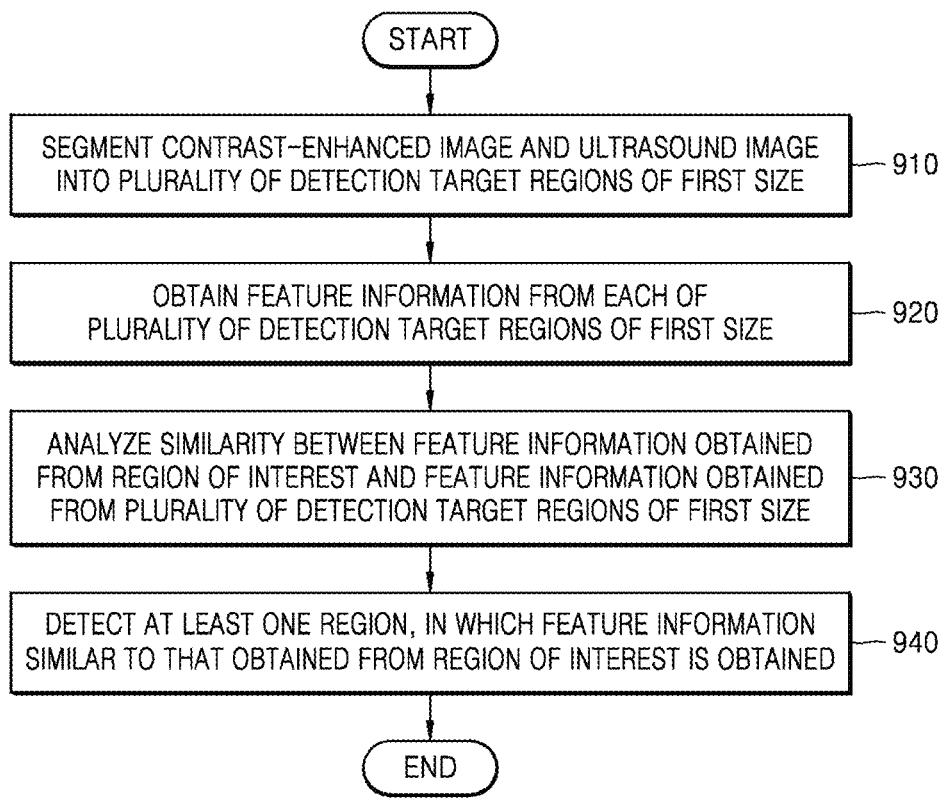
FIG. 9 is a flowchart illustrating a method of controlling an ultrasound imaging apparatus according to an embodiment of the present disclosure.

FIG. 9 is a flowchart illustrating a method of controlling the ultrasound imaging apparatus 300 according to the operation 430.

According to the embodiment of FIG. 9, the operation of detecting at least one region, in which the feature information similar to that of the region of interest, by the ultrasound imaging apparatus 300 may include segmenting the contrast-enhanced image and the ultrasound image into a plurality of detection target regions of the first size (910), obtaining feature information from each of the plurality of detecting target regions of the first size (920), analyzing similarity between the feature information obtained from the region of interest and the feature information obtained from the plurality of detection target regions of the first size (930), and detecting at least one region, in which the feature information similar to that of the region of interest is obtained (940).

In operation 910, the ultrasound imaging apparatus 300 may segment the contrast-enhanced image and the ultrasound image into the plurality of detection target regions having the first size.

According to the embodiment, the detection target region of the first size segmented by the ultrasound imaging apparatus 300 may have an equal size to that of the region of interest. Since the detection target region having the first size is segmented to have the same size as the region of interest, speed and accuracy of detecting the region, in which the feature information similar to the region of interest is obtained, may be improved.

According to the embodiment, when the region, in which the feature information similar to that of the region of interest is detected, the ultrasound imaging apparatus 300 may segment the detected region into a plurality of detection target regions of a second size.

According to the embodiment, the ultrasound imaging apparatus 300 may segment the contrast-enhanced image and the ultrasound image into the plurality of detection target regions having the first size to overlap one another. The plurality of detection target regions of the first size segmented by the ultrasound imaging apparatus 300 may overlap with one another by an area equal to or smaller than the first size.

The operation 910 according to the embodiment will be additionally described later with reference to FIGS. 10, 12, and 13.

In addition, in operation 920, the ultrasound imaging apparatus 300 may obtain feature information from each of the plurality of detection target regions of the first size. For example, the ultrasound imaging apparatus 300 may obtain the feature information of the contrast-enhanced image and the ultrasound image from each of the plurality of detection target regions of the first size.

According to the embodiment, the ultrasound imaging apparatus 300 may obtain the feature information of the contrast-enhanced image from each of the plurality of detection target regions of the first size. For example, the ultrasound imaging apparatus 300 may generate a time intensity curve representing a variation in the intensity of a contrast-enhanced signal transmitted from each of the plurality of detection target regions of the first size, based on the contrast-enhanced signal. The ultrasound imaging apparatus 300 may obtain the feature information of the contrast-enhanced image by using the generated time intensity curve. The ultrasound imaging apparatus 300 may obtain feature information of each of the plurality of detection target regions of the first size by using the parameter obtained from the generated time intensity curve.

According to the embodiment, the ultrasound imaging apparatus 300 may obtain the feature information of the ultrasound image from each of the plurality of detection target regions of the first size. For example, the ultrasound imaging apparatus 300 may obtain the feature information of each of the plurality of detection target regions of the first size by using the intensity of the ultrasound image signal transmitted from each of the plurality of detection target regions of the first size.

According to the embodiment, the ultrasound imaging apparatus 300 may obtain the feature information of the contrast-enhanced image and the ultrasound image from each of the plurality of detection target regions of the first size. For example, the ultrasound imaging apparatus 300 may obtain the feature information by using the time intensity curve representing the variation in the intensity of the contrast-enhanced signal transmitted from each of the plurality of detection target regions of the first size and the intensity of the ultrasound image signal.

In addition, since operation 920 is similar to operation 510 and operation 520, detailed descriptions thereof are omitted.

In addition, in operation 930, the ultrasound imaging apparatus 300 may analyze similarity between the feature information obtained from the region of interest and the feature information obtained from the plurality of detection target regions of the first size.

Operation 930 according to the embodiment will be additionally described with reference to FIG. 10.

In operation 940, the ultrasound imaging apparatus 300 may detect at least one region, in which feature information similar to that of the region of interest is obtained.

Operation 940 according to the embodiment will be described additionally with reference to FIG. 10.

Figure 10:
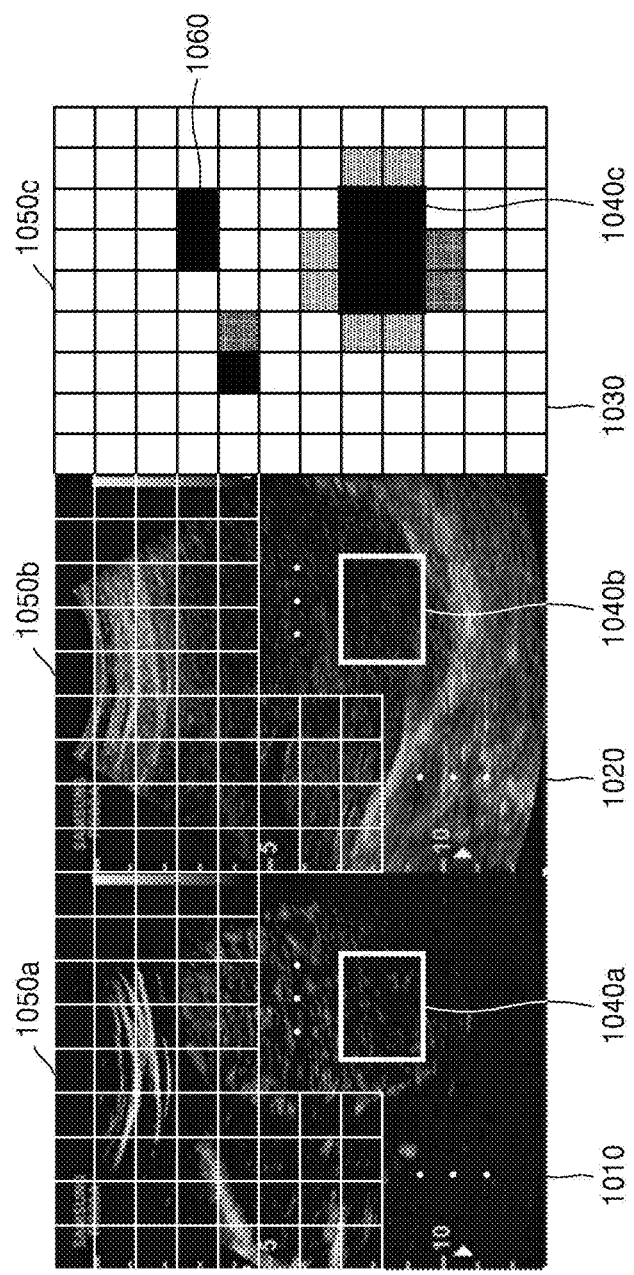
FIG. 10 is a diagram illustrating detection of regions having similar feature information by an ultrasound imaging apparatus according to an embodiment of the present disclosure.

In addition, FIG. 10 is a diagram showing operations 910, 930, and 940 according to the embodiment detecting regions having similar feature information.

According to operation 910 of the embodiment, the ultrasound imaging apparatus 300 may segment a contrast-enhanced image 1010 and an ultrasound image 1020 into a plurality of detection target regions 1050a and 1050b having a first size.

According to the embodiment illustrated in operation 930, the ultrasound imaging apparatus 300 may analyze similarity between feature information obtained from each of the detection target regions 1050a of the first size segmented from the contrast-enhanced image 1010 and feature information obtained from a region of interest 1040a.

The ultrasound imaging apparatus 300 may analyze similarity between feature information obtained from each of the plurality of detection target regions 1050b of the first size segmented from the ultrasound image 1020 and the feature information obtained from the region of interest 1040b.

The ultrasound imaging apparatus 300 may generate a similarity map 1030 representing a result of analyzing the similarity between the feature information obtained from the regions of interest 1040a and 1040b and the feature information obtained from each of the plurality of detection target regions 1050a and 1050b of the first size.

The ultrasound imaging apparatus 300 may generate the similarity map 1030 so that a region 1050c corresponding to the detection target regions of the first size segmented from the contrast-enhanced image 1010 and the ultrasound image 1020 may be included in the similarity map 1030.

In operation 940 according to the embodiment, the ultrasound imaging apparatus 300 may detect at least one region, in which feature information similar to that of the region of interest 1040a is obtained, by using a result of analyzing the similarity between the feature information obtained from each of the plurality of detection target regions 1050a of the first size segmented from the contrast-enhanced image 1010 and the feature information obtained from the region of interest 1040a.

The ultrasound imaging apparatus 300 may detect at least one region, in which feature information similar to that of the region of interest 1040b is obtained, by using a result of analyzing the similarity between the feature information obtained from each of the plurality of detection target regions 1050b of the first size segmented from the ultrasound image 1020 and the feature information obtained from the region of interest 1040b.

The ultrasound imaging apparatus 300 may detect at least one region 1060, in which feature information similar to that of the region of interest 1040c is obtained, by using the similarity map 1030.

In addition, FIG. 11 is a flowchart illustrating a method of controlling the ultrasound imaging apparatus 300 according to the operation 430.

According to the embodiment of FIG. 11, the operation of detecting at least one region, in which the feature information similar to that of the region of interest, by the ultrasound imaging apparatus 300 may include segmenting the contrast-enhanced image and the ultrasound image into a plurality of detection target regions of the first size (1110), obtaining feature information from each of the plurality of detecting target regions of the first size (1120), analyzing similarity between the feature information obtained from the region of interest and the feature information obtained from the plurality of detection target regions of the first size (1130), segmenting the at least one detected region into a plurality of detection target regions of a second size (1150), obtaining feature information from each of the plurality of detection target regions of the second size (1160), analyzing similarity between the feature information obtained from the region of interest and feature information obtained from the plurality of detection target regions of the second size (1170), and detecting at least one region, in which the feature information similar to that of the region of interest is obtained (1180).

Operation 1110 is similar to operation 910, and detailed descriptions thereof are omitted.

Operation 1120 is similar to operation 920, and detailed descriptions thereof are omitted.

Operation 1130 is similar to operation 930, and detailed descriptions thereof are omitted.

Operation 1140 is similar to operation 940, and detailed descriptions thereof are omitted.

In operation 1150, the ultrasound imaging apparatus 300 may segment at least one region, in which the feature information similar to that of the region of interest is obtained, into the detection target regions of the second size.

According to the embodiment, the plurality of detection target regions of the second size segmented by the ultrasound imaging apparatus 300 may overlap with one another. The plurality of detection target regions of the second size segmented by the ultrasound imaging apparatus 300 may overlap with one another by an area equal to or smaller than the second size.

Operation 1150 according to the embodiment will be described additionally with reference to FIG. 12.

In operation 1160, the ultrasound imaging apparatus 300 may obtain feature information from each of the plurality of detection target regions of the second size. Since operation 1160 is similar to operation 920 and operation 1120, detailed descriptions thereof are omitted.

In operation 1170, the ultrasound imaging apparatus 300 may analyze similarity between the feature information obtained from the region of interest and the feature information obtained from the plurality of detection target regions of the second size. Since operation 1170 is similar to operation 930 and operation 1130, detailed descriptions thereof are omitted.

In operation 1180, the ultrasound imaging apparatus 300 may detect at least one region, in which feature information similar to that of the region of interest is obtained. Since operation 1180 is similar to operation 940 and operation 1140, detailed descriptions thereof are omitted.

Figure 12A:
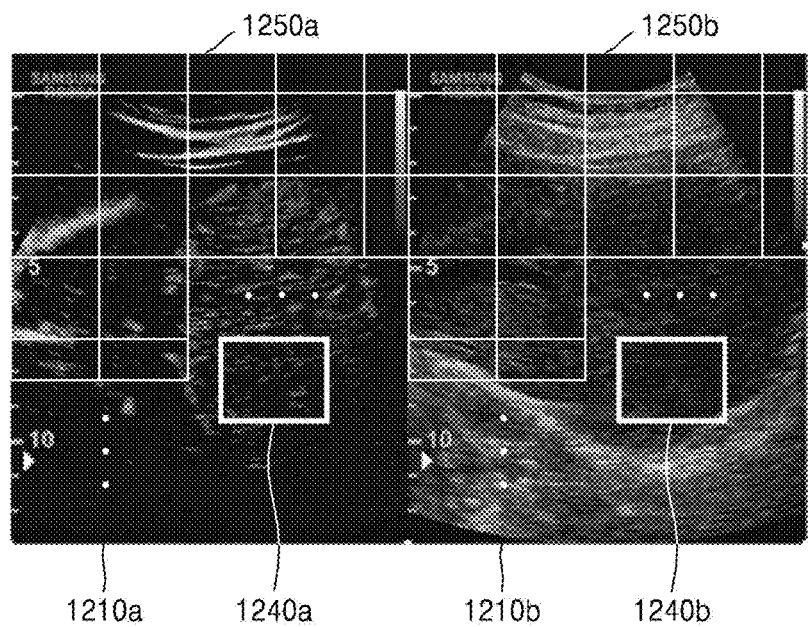
FIGS. 12A and 12B are diagrams illustrating detection of regions having similar feature information by an ultrasound imaging apparatus according to an embodiment of the present disclosure.
Figure 12B:
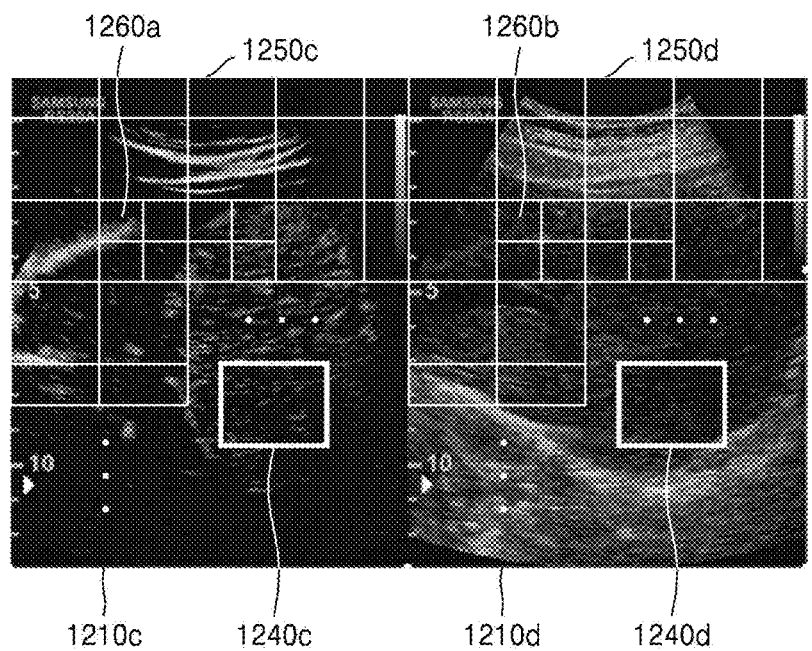

In addition, FIG. 12 is a diagram showing operations 910 and 1150 according to the embodiment detecting regions having similar feature information.

According to operation 910 of the embodiment, the ultrasound imaging apparatus 300 may segment a contrast-enhanced image 1210a and an ultrasound image 1220a into a plurality of detection target regions 1250a and 1250b having a first size. When a region having the feature information similar to that of a region of interest 1240a or 1240b is obtained, the ultrasound imaging apparatus 300 may segment detected regions of the contrast-enhanced image 1210b and the ultrasound image 1220b into detection target regions 1260a and 1260b of the second size.

In operation 1150 according to the embodiment, when at least one region, in which the feature information similar to that of the region of interest 1240a or 1240b is obtained, is detected from the plurality of detection target regions 1250a and 1250b of the first size, the ultrasound imaging apparatus 300 may segment the detected region of the contrast-enhanced image 1210a and the ultrasound image 1220b into the plurality of detection target regions 1260a and 1260b of the second size.

Figure 13:
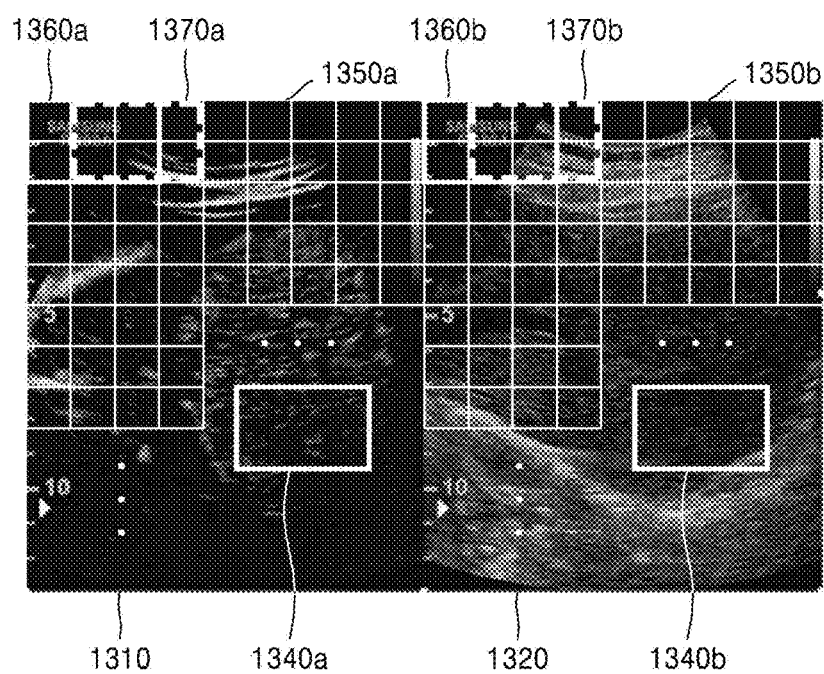
FIG. 13 is a diagram illustrating detection of regions having similar feature information by an ultrasound imaging apparatus according to an embodiment of the present disclosure.

In addition, FIG. 13 is a diagram showing operation 910 according to the embodiment detecting regions having similar feature information.

In operation 910 according to the embodiment, the ultrasound imaging apparatus 300 may segment a contrast-enhanced image 1310 and an ultrasound image 1320 into a plurality of detection target regions 1360a, 1370a, 1360b, and 1370b of the first size. The ultrasound imaging apparatus 300 may segment the contrast-enhanced image 1310 into the plurality of detection target regions 1360a and 1370a of the first size to overlap with each other. The ultrasound imaging apparatus 300 may segment the ultrasound image 1320 into the plurality of detection target regions 1360b and 1370b of the first size to overlap with each other. Detection target regions 1360a and 1360b are shown with a solid line and detection target regions 1370a and 1370b are shown with a dashed line.

Figure 14:
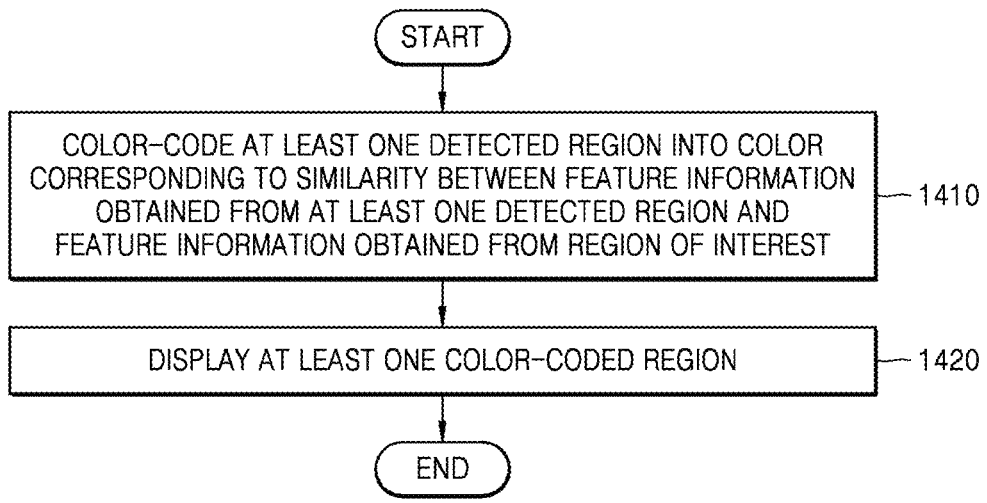
FIG. 14 is a flowchart illustrating a method of controlling an ultrasound imaging apparatus according to an embodiment of the present disclosure.

FIG. 14 is a flowchart illustrating a method of controlling the ultrasound imaging apparatus 300 in operation 440 according to the embodiment.

According to the embodiment illustrated with reference to FIG. 14, the displaying of the at least one detected region, in which the feature information similar to that of the region of interest is obtained, in the ultrasound imaging apparatus 300 may include color-coding the at least one detected region into a color corresponding to the similarity between the feature information obtained from the at least one region and the feature information obtained from the region of interest (1410), and displaying the color-coded at least one region (1420).

In operation 1410, the ultrasound imaging apparatus 300 may color-code the at least one detected region into a color corresponding to the similarity between the feature information obtained from the at least one detected region and the feature information obtained from the region of interest.

According to the embodiment, as the similarity between the feature information obtained from the at least one detected region and the feature information obtained from region of interest increases, the ultrasound imaging apparatus 300 may color-code the at least one detected region into a color (e.g., orange) similar to a preset color (e.g., red). In other words, the similarity between the displayed colors may be commensurate with the similarity between the feature information obtained from the at least one detected region and the feature information obtained from the region of interest.

Operation 1410 according to the embodiment will be described additionally with reference to FIG. 15.

In operation 1420, the ultrasound imaging apparatus 300 may display the color-coded at least one region.

According to the embodiment, the ultrasound imaging apparatus 300 may display a contour line of the at least one detected region on at least one of the contrast-enhanced image and the ultrasound image.

Operation 1420 according to the embodiment will be described additionally with reference to FIG. 15.

Figure 15:
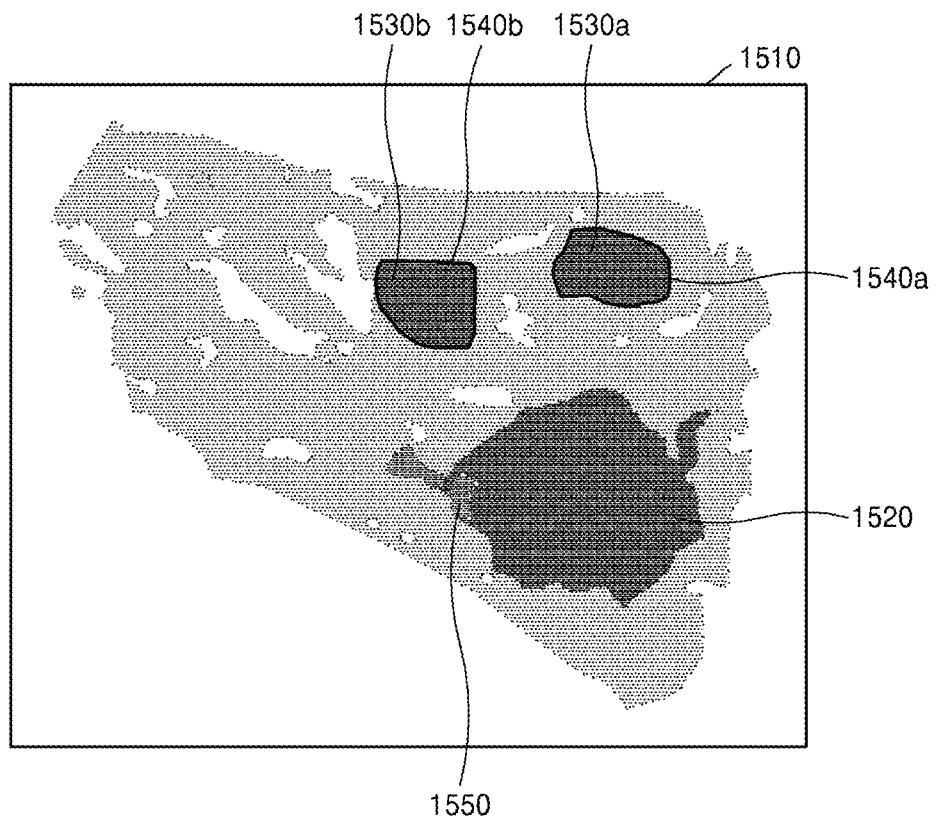
FIG. 15 is a diagram illustrating color-coding of a region having similar feature information to that of a region of interest performed by an ultrasound imaging apparatus according to an embodiment of the present disclosure.

FIG. 15 is a diagram showing a color-coding of a region having similar feature information to that of the region of interest in the ultrasound imaging apparatus 300 in operations 1410 and 1420 according to the embodiment of the present disclosure.

In operation 1410 according to the embodiment, the ultrasound imaging apparatus 300 may color-code at least one detected region 1530a and 1530b, in which feature information similar to that of a region of interest 1520 of a contrast-enhanced image 1510 is obtained, into the same color as the region of interest (e.g., red). The ultrasound imaging apparatus 300 may color-code at least one region 1550, in which feature information different from that of the region of interest 1520 is obtained, into a complementary color (e.g., blue) of the region of interest 1520.

In operation 1420 according to the embodiment, the ultrasound imaging apparatus 300 may display contour lines 1540a and 1540b of the at least one region 1530a and 1530b, in which feature information similar to that of the region of interest 1520 is obtained, on the contrast-enhanced image 1510.

Since the ultrasound imaging apparatus 300 displays at least one region, in which feature information similar to that of the set region of interest is obtained, on at least one of the contrast-enhanced image and the ultrasound image, the user may easily detect a lesion that may not be easily identified with the naked eye. Also, the user's mistake of not finding a lesion may be prevented. In addition, although the user is not skilled in using the ultrasound imaging apparatus 300, the user may easily detect a lesion in the image.

The embodiments provided herein may be implemented in the form of a computer-readable recording medium for storing computer-executable commands and data. The above commands may be stored in the form of program codes, and when being executed by a processor, a predetermined program module may be generated to perform a predetermined operation. Also, the above commands, when being executed by the processor, may perform predetermined operations of the embodiments provided herein.

It should be understood that embodiments described herein should be considered in a descriptive sense only and not for purposes of limitation. Descriptions of features or aspects within each embodiment should typically be considered as available for other similar features or aspects in other embodiments.

While one or more embodiments have been described with reference to the figures, it will be understood by those of ordinary skill in the art that various changes in form and details may be made therein without departing from the spirit and scope as defined by the following claims.

What is claimed is:

1. A method of controlling an ultrasound imaging apparatus by executing at least one instruction stored in a memory of the ultrasound imaging apparatus, the method comprising:
   acquiring a contrast-enhanced image and a B mode ultrasound image using a signal received through a probe from an object;
   displaying the contrast-enhanced image of the object and the B mode ultrasound image of the object that are matched on a display of the ultrasound imaging apparatus;
   setting a first region of interest including a lesion in the B mode ultrasound image of the object;
   identifying, from the contrast-enhanced image of the object, a second region of interest interest, including the lesion, corresponding to the first region of interest;

obtaining feature information of the lesion from the second region of interest;

detecting a first region, from the contrast-enhanced image of the object, including other feature information similar to the feature information of the lesion obtained from the second region of interest by comparing the feature information of the second region of interest with feature information of other regions of the contrast-enhanced image, wherein the first region is at a different location from the second region of interest in the contrast-enhanced image of the object; and identifying, from the B mode ultrasound image of the object, a second region corresponding to the first region; and displaying the first region on the contrast-enhanced image of the object and the second region on the B mode ultrasound image of the object, wherein the obtaining the feature information of the lesion comprises:

generating a first time intensity curve, representing a variation in an intensity of a contrast-enhanced signal according to time, corresponding to the second region of interest; and obtaining the feature information of the lesion from the second region of interest by extracting first parameters from the first time intensity curve, and wherein the detecting of the first region comprises:

segmenting the contrast-enhanced image of the object into a plurality of first detection target regions having a first size;

generating a plurality of second time intensity curves corresponding to each of the plurality of first detection target regions obtaining first target feature information from each of the plurality of first detection target regions by extracting a plurality of second parameters from each of the plurality of second time intensity curve;

analyzing a similarity between the feature information obtained from the second region of interest and the first target feature information obtained from each of the plurality of first detection target regions having the first size by comparing the first parameters with each of the plurality of second parameters; and detecting the first region, by using a result of the analysis.

2. The method of claim 1, wherein the detecting of the first region by using the result of the analysis comprises:

segmenting the plurality of first detection target regions having the first size into a plurality of second detection target regions having a second size;

obtaining second target feature information from each of the plurality of second detection target regions having the second size;

analyzing a similarity between the feature information obtained from the second region of interest and the second target feature information obtained from each of the plurality of second detection target regions having the second size; and detecting the first region from the plurality of second detection target regions by using a result of the analysis.

3. The method of claim 1, wherein the first size of the plurality of first detection target regions is equal to a size of the second region of interest.

4. The method of claim 1, wherein the segmenting of the contrast-enhanced image of the object into the plurality of first detection target regions having the first size comprises segmenting the contrast-enhanced image of the object into the plurality of first detection target regions having the first size so that the plurality of first detection target regions overlap with one another by an area smaller than the first size.

5. The method of claim 1, wherein the displaying of the first region and the second region comprises:

color-coding the first region and the second region; and displaying the color-coded first region on the contrast-enhanced image of the object and the color-coded second region on the ultrasound image.

6. The method of claim 5, wherein the color-coding of the first region and the second region comprises:

color-coding each of the first region and the second region into a preset color corresponding to a similarity between the feature information obtained from each of the first region and the second region and the feature information obtained from the second region of interest.

7. The method of claim 1, wherein the displaying of the first region and the second region comprises:

displaying a contour line of the first region on the contrast-enhanced image of the object and the second region on the B-mode ultrasound image of the object.

8. An ultrasound imaging apparatus comprising:

a probe configured to receive signal from an object;

a display;

an input interface configured to receive a user input;

a memory storing at least one instruction;

at least one processor configured to execute the at least one instruction to:

generate a contrast-enhanced image of the object and an B-mode ultrasound image of the object using the signal received through the probe, and to match the contrast-enhanced image and the B-mode ultrasound image of the object;

control the display to display the contrast-enhanced image of the object and the B-mode ultrasound image of the object; and control the input interface to receive an input signal for setting a first region of interest including a lesion in the B-mode ultrasound image of the object, set the first region of interest including a lesion in the B-mode ultrasound image of the object based on the input signal for setting a first region of interest, identify, from the contrast-enhanced image of the object, a second region of interest including a lesion corresponding to the first region of interest, obtain feature information of the lesion from the second region of interest, detect a first region, from the contrast-enhanced image of the object, including other feature information similar to the feature information obtained from the second region of interest by comparing the feature information of the second region of interest with feature information of other regions of the contrast-enhanced image, wherein the first region is a different location from the second region of interest in the contrast-enhanced image of the object, identify, from the B-mode ultrasound image of the object, a second region corresponding to the first region, and control the display to display the first region on the contrast-enhanced image of the object and the second region on the B-mode ultrasound image of the object, wherein the at least one processor is further configured to execute to the at least one instruction to:

generate a first time intensity curve representing a variation in an intensity of a contrast-enhanced signal according to time, corresponding to the second region of interest and obtain the feature information of the lesion from the second region of interest by extracting first parameters from the first time intensity, wherein the at least one processor is further configured to execute to the at least one instruction to:

segment the contrast-enhanced image of the object into a plurality of first detection target regions having a first size, generate a plurality of second time intensity curves corresponding to each of the plurality of first detection target regions, obtain first target feature information from each of the plurality of first detection target regions by extracting a plurality of second parameters from each of the plurality of second time intensity curve, analyze a similarity between the feature information obtained from the second region of interest and the first target feature information obtained from each of the plurality of first detection target regions having the first size by comparing the first parameters with each of the plurality of second parameters, and detect the first region by using a result of the analysis.

9. The ultrasound imaging apparatus of claim 8, wherein the at least one processor is further configured to execute the at least one instruction to:

segment the plurality of first detection target regions having the first size into a plurality of second detection target regions having a second size, obtain second target feature information from each of the plurality of second detection target regions having the second size, analyze a similarity between the feature information obtained from the second region of interest and the second target feature information obtained from each of the plurality of second detection target regions having the second size, and detect the first region from the plurality of second detection target regions by using a result of the analysis.

10. The ultrasound imaging apparatus of claim 8, wherein the first size of the plurality of first detection target regions is equal to a size of the second region of interest.

11. The ultrasound imaging apparatus of claim 8, wherein the at least one processor is further configured to execute the at least one instruction to segment the contrast-enhanced image so that the plurality of first detection target regions having the first size overlap with one another by an area smaller than the first size.

12. The ultrasound imaging apparatus of claim 8, wherein the at least one processor is further configured to execute the at least one instruction to color-code the first region and the second region, and the display is further configured to display the color-coded first region on the contrast-enhanced image of the object and the second region on the B-mode ultrasound image of the object that are color-coded.

13. The ultrasound imaging apparatus of claim 12, wherein the at least one processor is further configured to execute the at least one instruction to:

color-code each of the first region and the second region into a preset color corresponding to a similarity between the feature information obtained from each of the first region and the second region and the feature information obtained from the second region of interest.

14. The ultrasound imaging apparatus of claim 8, wherein the at least one processor is further configured to execute the at least one instruction to display a contour line of the first region on the contrast-enhanced image of the object and the second region on the B-mode ultrasound image of the object.

* * * * *

UNITED STATES PATENT AND TRADEMARK OFFICE
CERTIFICATE OF CORRECTION

| | | |
|---|---|---|
| PATENT NO. | : 11,096,667 B2 | Page 1 of 1 |
| APPLICATION NO. | : 15/814708 | |
| DATED | : August 24, 2021 | |
| INVENTOR(S) | : Jong-geun Park et al. | |

It is certified that error appears in the above-identified patent and that said Letters Patent is hereby corrected as shown below:

In the Claims

In Claim 1, Column 18, Line 66, delete "interest"

Signed and Sealed this
Thirty-first Day of December, 2024

Derrick Brent
*Acting Director of the United States Patent and Trademark Office*